United States Patent
Robrahn et al.

[11] Patent Number: 6,138,285
[45] Date of Patent: Oct. 31, 2000

[54] GOGGLE FOR SPORTS AND ADVERSE ENVIRONMENTS

[75] Inventors: David T. Robrahn, Ketchum, Id.; Robert Youmans, Vashon, Wash.

[73] Assignee: Scott USA, Inc., Sun Valley, Id.

[21] Appl. No.: 09/262,809

[22] Filed: Mar. 5, 1999

[51] Int. Cl.[7] .................................................. A61F 9/02
[52] U.S. Cl. ..................................................... 2/436; 2/434
[58] Field of Search ................................. 2/9, 171.3, 426, 2/428, 434, 436, 437

[56] References Cited

U.S. PATENT DOCUMENTS

| | | |
|---|---|---|
| 2,409,286 | 10/1946 | Joyce . |
| 3,368,221 | 2/1968 | Anderson . |
| 3,395,406 | 8/1968 | Smith . |
| 3,718,937 | 3/1973 | Smith . |
| 3,945,044 | 3/1976 | McGee et al. . |
| 4,149,276 | 4/1979 | Castro . |
| 4,571,748 | 2/1986 | Carroll et al. . |
| 4,653,124 | 3/1987 | McNeal et al. . |
| 4,977,627 | 12/1990 | Metcalfe et al. . |
| 5,363,512 | 11/1994 | Grabos, Jr. et al. . |

*Primary Examiner*—John J. Calvert
*Assistant Examiner*—Katherine Moran
*Attorney, Agent, or Firm*—Jenner & Block

[57] ABSTRACT

A goggle has a replaceable lens mounted in a flexible frame containing several large air vents facing forwardly to input external air into the goggle interior. The inlet air vents have converging and angled walls. A first porous foam of particular porosity covers the inlet air vents and is located in an upper air channel with a curved deflector wall to disperse the external air into the interior space. Exit vents located in the bottom of the frame are covered with a second porous foam of different characteristics than the first porous foam. The sides of the goggle frame include curved slots with curved retention bars around which a stretchable headband strap is secured to create uneven load forces on the sides of the goggle frame.

46 Claims, 3 Drawing Sheets

HIGHEST LOADS
LOWEST LOAD

GOGGLE FOR SPORTS AND ADVERSE ENVIRONMENTS

TECHNICAL FIELD

This invention relates to a goggle used primarily in an outdoor or other adverse environment, such as a ski goggle or a motorcycle goggle or a safety goggle. It has applicability to goggles having air vents to circulate outside air through the interior of the goggle. It has particular utility for goggles formed by a plastic flexible frame with a replaceable lens, but is not limited to such use.

BACKGROUND OF THE INVENTION

Goggles which are intended for use in an outdoor environment include ski goggles, motorcycle goggles and the like as well as safety goggles which provide protection for the wearer's eyes from external air and particulate matter. Such goggles typically have vent apertures open to external air flow to exchange air between the exterior environment and the interior of the goggle. Such a vented exchange of air will minimize fogging caused by moisture in the air condensing on the lens of the goggle. The vent apertures are typically covered by a porous foam to control the air exchange while forming a partial barrier to snow, dust and other particulate matter. Typical goggles also include a replaceable lens which may be a single lens or a double lens, and often such lenses are tinted in various colors to assist in contrast and glare protection.

Numerous goggles have vent apertures in the top, bottom and/or sides of the frame, which apertures are covered in a porous foam, in order to vent the goggle interior to exterior air. Vent apertures which face forwardly into the direct air flow stream are known and include goggles with apertures in the lens as well as goggles with apertures in the top sections of the frame. In general, such forward facing apertures are of small diameter because too great a volume of air flow into the goggle interior can be deltirious to the wearer's eyes and can cause tearing of the eyes due to the air flow as well as due to cold exterior temperatures such as exist in a ski goggle. In many instances, these forward facing aperture holes do not communicate directly with the interior of the goggle, but rather create a venturi effect to draw air out of the goggle interior. In general, the amount of air flow through the interior of such goggles was relatively small notwithstanding that an increased rate of air exchange could improve the anti-fogging properties of the goggle. As a result, a balance was needed between increased air flow through goggle vents and the various adverse effect which were the consequence of increased air flow.

Another problem with prior goggles having a plastic flexible frame is that tension in a stretchable headband strap can distort the goggle frame. Any distortion can alter the characteristics of the goggle against the wearer's face as well as the fit within a helmet. Furthermore, the helmet may include padding associated with the front opening which can interfere with the vent apertures in a typical vented goggle and render ineffective such venting. Many goggles with vent apertures are not fully effective when used in conjunction with a helmet.

SUMMARY OF THE PRESENT INVENTION

A goggle is provided which overcomes certain of the problems and disadvantages of prior goggles. Many of its features are useful when a goggle is worn in conjunction with a helmet, although the goggle is not limited to use with a helmet. Other features overcome problems associated with goggles intended to be used in a high speed sport, as well as problems associated with an outdoor or other adverse environment which is prone to a wide variety of atmospheric conditions such as to create fogging on the lens.

In one aspect, the invention has particular utility to goggles used in an outdoor environment where air may be rapidly moving in relative motion toward the goggle, due either to the movement of the wearer and/or external air flow toward the user. Unlike prior approaches to venting a goggle interior, the goggle includes large vent openings which face forwardly to directly admit large volumes of external air. Furthermore, these air volumes are increased in speed as they enter the goggle frame rather than being of similar or reduced speed as has been typical in the past. For certain embodiments, the result is an increased rate of evaporation of moisture from an inside surface of the lens, but without the deltirious effects upon the wearer's eyes which could otherwise result from large air scoops which face forwardly. This volume of interior air can be controlled and disbursed in ways not previously possible to improve the overall venting characteristics of the goggle. While not limited to such use, this goggle provides improved venting characteristics when worn in conjunction with a helmet which might otherwise block or interfere with portions of the vents for typical prior art goggles.

In another aspect, the goggle is formed of a flexible plastic frame and has an improved retention strap mechanism which prevents distortion and improves fit and comfort as well as contributing to a longer life and better fit for the flexible goggle frame. This is particularly useful when the goggle is used in conjunction with a helmet where the strap can be adjusted for tight retention.

A better understanding of the present invention along with other objects and advantages will become apparent in the following description and with reference to the following drawings.

DESCRIPTION OF THE PREFERRED EMBODIMENTS

Figure 1:
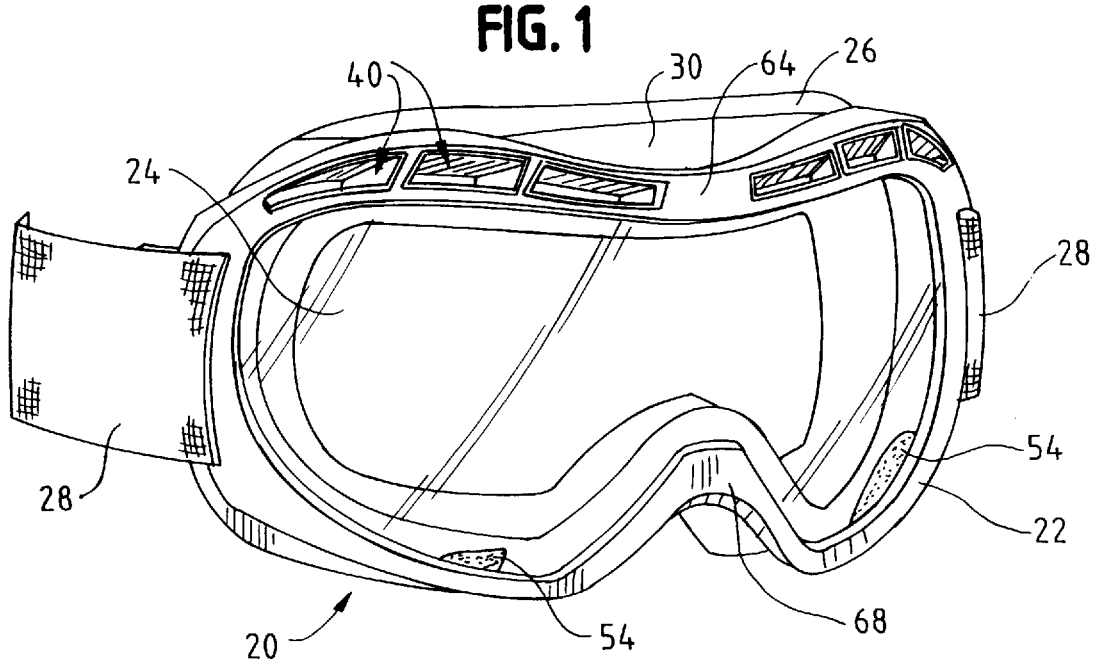
FIG. 1 is a perspective view of the novel goggle.

As seen in the drawings, a goggle 20 which is particularly useful in an outdoor environment, although not limited thereto, includes a plastic flexible frame 22 which surrounds the eye region of a wearer. A front lens 24 is removably mounted at the forward area of the surrounding frame 22 in order to protect the wearer's eyes. A flexible face padding 26 is glued or otherwise affixed to the rear of the frame 22 in order the cushion the frame against the face of the wearer and create a partial seal against the wearer's face. An elastic headband strap 28 attaches to both sides of the frame 22 to secure the goggle to the wearer's head or to the back of a helmet, as appropriate. Typically, the strap 28 will include a buckle adjustment (not illustrated) in order to vary the length of the strap 28 so as to secure the goggle relatively snugly against the face of the wearer.

The flexible frame 22 includes a top portion 30, a bottom portion 32, and side portions 34 which are injection molded as one piece and are pliable while being relatively stiff as is conventional in vented sports goggles. The frame surrounding portions in conjunction with the front lens 24 define an interior space 36, see FIG. 3, when the goggle is placed against the wearer's face.

Figure 2:
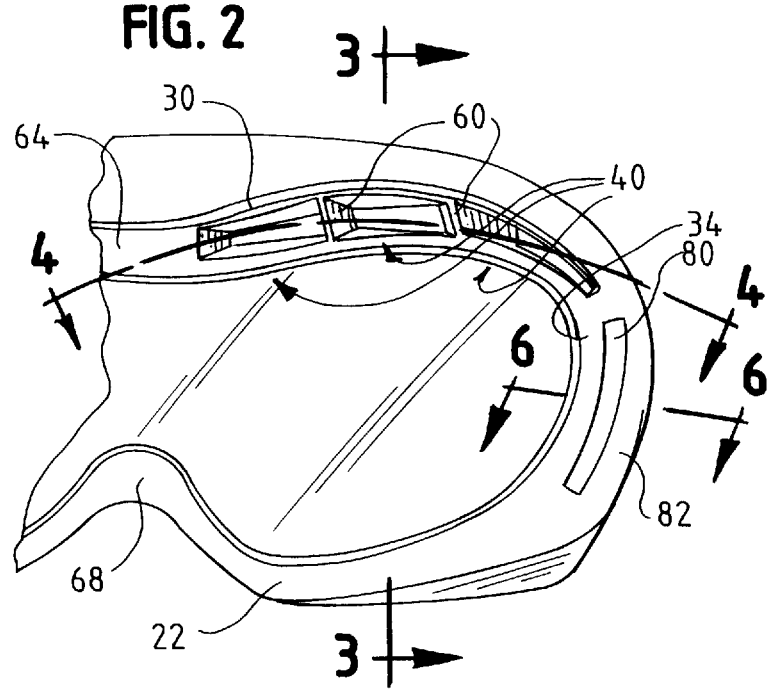
FIG. 2 is a front plane view of a portion of the goggle of FIG. 1 with the headband strap removed to better show the side retention mechanism.
Figure 3:
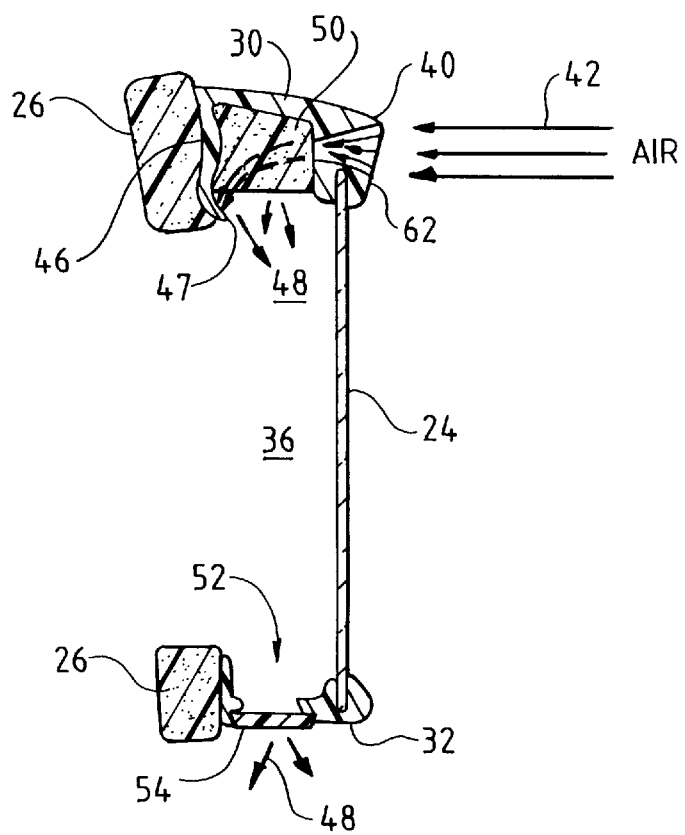
FIG. 3 is a side cross-sectional view of the goggle taken along lines 3—3 of FIG. 2.

As is seen best in FIGS. 1–3, the top portion 30 of the goggle frame is solid and has a generally smooth and planar extent, which can dip in the center. This smooth, solid, top surface forms a helmet contacting or mating surface for use when the goggle is worn in conjunction with a helmet. There are no vent apertures or other openings in the top portion 30. When a helmet is worn, the top planar surface will mate with and contact the helmet or helmet padding, in order to form a partial seal between the goggle top where it abuts the helmet. As a result, the goggle is particularly adapted for use with a helmet, although it is not limited to such use. The frame side portions 34 and/or bottom portion 32 have air vents located therein for purposes of exiting air flowing out of the goggle interior, as will be explained.

Along an elongated front upper section of the frame, beneath the top portion 30, a plurality of forward facing air scoops or air vents 40 are located to directly receive air as the wearer moves relatively in a forward direction. This frontal air, illustrated by the arrows 42 in FIGS. 3 and 4, enters the forwardly facing air scoops 40 in large volumes compared to prior art vented goggles as the wearer is relatively moving in a forward direction, such as across a ski slope or on a vehicle such as a motorcycle or snowmobile. The frontal air 42 is funneled through the large vent scoops 40 and into an elongated upper chamber 44, see FIG. 4, enclosed along its top, rear and sides and which is open downwardly at its bottom to channel the frontal air into the goggle interior region 36. The upper chamber 44 includes means for dispersing the air flow generally downward and includes a forward component to improve interior venting of the goggle but without rapid air flow across the wearer's eyes.

This dispersing mechanism can take several forms which can be combined or can be separately provided, as follows. It includes in part the shape of the upper chamber 44 including a rear wall 46 spaced from and located oppositely the exit openings of the forward vents 40. The rear wall 46 terminates in a bottom curved deflector 47which is curved forwardly to redirect some of the frontal air 42 so as to have a forward component towards the inside of the front lens 24. In addition, a permeable foam 50 is located in the upper chamber 44 in contact with the air scoops 40 and is of a porosity and size, as will be explained, to redirect and disburse the air flow from the forward facing inlet vents so as to have a reduced velocity and volume which flows in a disbursed manner into the interior space 36 of the goggle.

Figure 4:
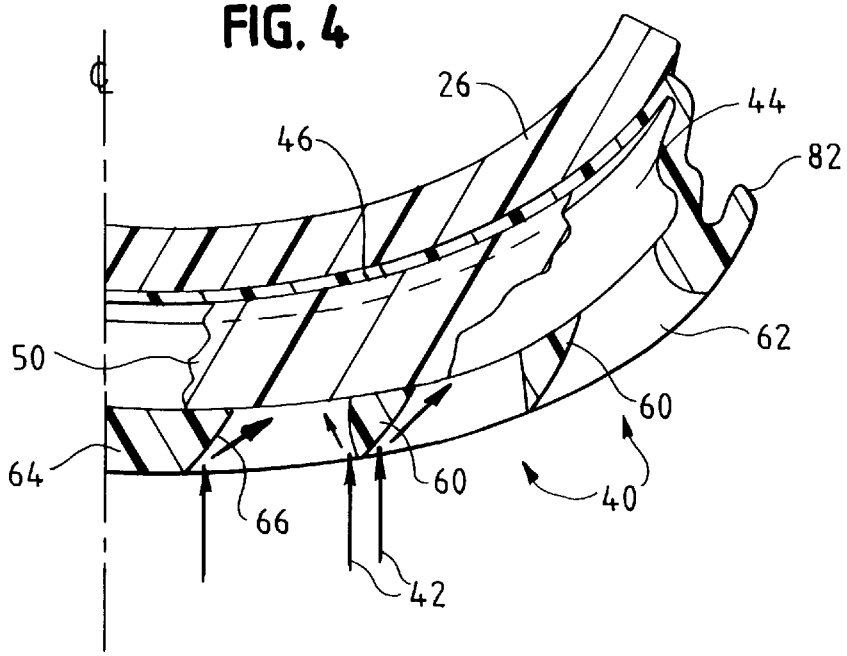
FIG. 4 is a top cross-sectional view of a portion of the goggle taken substantially along lines 4—4 of FIG. 2.

In one embodiment, the foam 50 for the forward inlet vents is a thick foam strip as illustrated in FIGS. 3 and 4. Such a thick foam strip may fill a substantial portion or all of the upper chamber 44. The dimensions of such foam, by way of example, can be approximately 16 mm by 16 mm by the longitude length of the upper chamber 44. The foam strip 50 does not have to occupy the entire volume of the upper chamber, but should be in intimate contact with the exit openings of the plurality of air scoops 40 so that frontal air is directed into the interior volume of the foam strip 50. The foam strip 50 is formed of an open cell foam having, by way of example, a porosity of 20 to 80 pores per inch (ppi). A lower total porosity, such as 20 ppi, will admit more air flow into the goggle interior. A more dense foam, such as 80 ppi, will admit less air and can be selected to block most air from entering the goggle interior. A thick foam 50 of such dimensions and porosity serves to control the air flow and disburse it downwardly in a more even flow throughout the interior of the goggle space 36. As will appear, the thick foam 50 is preferably different than the porous foam used for the exit air vents, as will be explained.

With the use of such a thick foam 50, the curved deflector 47 can be eliminated, if desired, so that the rear wall 46 terminates in a more downward direction. The reason for eliminating the curved deflector 47 is that relatively little air will travel to the rear wall 46 when the foam 50 fills all or a substantial portion of the upper air chamber, and the elimination of the curved deflector 47 can simplify the injection molding process. Nonetheless, some air is filtered to the rear wall 46 and the curved deflector 47 can be retained if desired.

In another embodiment, the permeable foam strip 50 can be of thin dimensions (not illustrated) and can be glued or secured over the inside openings of the air scoops 40. For example, it can be an open cell foam of 3 mm (which is on the order of 0.120 inches) having a porosity of 80 pores per inch (ppi). Such an open cell foam of these characteristics is commonly used to cover air vents in sports goggles and is designed to prevent snow or other particulates from entering through the air vents into the interior of the goggle. If such a thin foam 50 is utilized in the upper chamber 44, then preferably the rear wall 46 terminates in the curved deflector 47. The frontal air will travel through such thin foam with relatively little obstruction, and therefore the curved deflector 47 is helpful to disperse the frontal air downwardly and with a forward component toward the front lens 24. This will assist in keeping the air flow out of the wearer's eyes. Such an embodiment using a thin foam 50 is useful for a smaller size goggle frame as well as for a more inexpensive goggle, as will appear.

The disbursed and reduced velocity air flow from the upper chamber 44 moves in a generally downward direction through the interior space 36 and partly against the inside of the front lens 24. This air moves towards a plurality of exit vents 52 located in the frame bottom 32. The exit vents 52 are formed as one or a plurality of large apertures in the goggle frame. Preferably, the exit vents 52 are located in the bottom section 32 of the goggle frame so as to draw air from the top of the frame downwardly in order to exit at the bottom of the frame in the vicinity of the nose region. This serves to disperse moisture-laden air from the wearer's nose and thus assist in reducing fogging within the goggle. However, the exit apertures 52 also can be located in the side regions of the frame, in place of or in addition to the exit vents in the bottom section.

The exit vents 52 are covered with a thin permeable foam strip 54 which can be of 3 mm thickness and having an open cell porosity of 80 ppi. Such a thin foam strip 54 of these dimensions is commonly used in prior art vented sports goggles to cover all of the vent apertures of the frame, including inlet vents as well as outlet vents. The total porosity of such thin foam presents minimal obstruction to the air flow but serves to minimize the entrance of snow and other particles into the interior of the goggle frame.

In a preferred embodiment useful for higher performance goggles, the top foam 50 which covers the entrance vents is different than the bottom foam 54 which covers the exit vents. In particular, the top foam 50 is of relatively thick size and has a different porosity characteristic than the bottom foam 54. The foam 50 is selected by the goggle designer to have an overall volume and porosity so that the total porosity through which the air will flow will cause a substantial decrease in velocity and volume of air flow and, in addition, will disburse the air in a variety of directions as it enters the interior space 36. In contrast, the bottom foam 54 should have a lessor total porosity so that air moves without substantial impediment through the exit vents. This requires that two different types of porous foam be utilized during assembly of the goggle. A first and more dense porous foam covers the input vents, and a second and less dense porous foam covers the exit vents.

To produce a more inexpensive goggle, and/or for a goggle of smaller size as might fit a child, it is possible to use the same foam strips for the entrance vents and the exit vents, although with reduced performance characteristics than the previous embodiment. However, this simplifies the manufacturing requirements in that the same foam is used for the entrance foam 50 and the exit foam 52. In such an embodiment, the upper chamber 44 should desirably be formed with the curved deflector 47 so as to redirect the frontal air which otherwise may have too great an inlet velocity and volume.

The inlet air scoops 40 are desirable of a large size and channel air from front openings through a continuously reducing volume to a small area exit opening contiguous with the upper chamber 44. This increases the velocity of the air flow as it moves through the front facing vents. In addition, the frontal air is redirected by the air scoops 40 so as to have a sideways directed component as the air moves through the scoops 40.

As seen in FIGS. 1–2, there are three large air vents or scoops 40 on the right side and three large air vents or scoops 40 on the left side of the upper section of the frame, although the specific number is merely exemplary. These plurality of forward facing inlet vents 40 encompass a substantial portion of the forward facing upper surface of the frame so as to admit substantial volumes of air. As seen in FIG. 2, the three scoops 40 are adjacent and are defined in part by the frame top wall 30, a pair of angled spacer walls 60, and a floor wall 62. Each spacer wall 62 is generally wedged-shaped in cross-section, as seen in FIG. 4, and has a substantial angle directed to the side so as to deflect frontal air 42 generally away from the center nose region of the goggle space. The upper center 64 of the frame above a center nose bridge 68 is solid and allows placement of a logo, if desired. The center region 64 terminates in an angled or wedge-shaped wall 66, see FIG. 4, which like the spacer walls 60 will deflect some of the frontal air away more towards the sides.

As seen in FIG. 4, each air scoop 40 has an entrance opening of large area at the front of the goggle which converges to a reduced area exit opening contiguous with the chamber 44. The top and bottom walls of the air scoops 40 are slanted and converge inwardly, as seen best in FIG. 3, so as to likewise reduce in area as the air moves from the front opening to the exit opening of the vents 40.

Each of the air vents 40 has an entrance opening which is elongated with its major axis of longer dimension than its minor axis. Each elongated entrance opening is generally of parallelogram shape but with a slightly curved shape. By way of example, the entrance opening of the center scoop seen in FIG. 2 can have a major axis length on the order of 22 mm and a minor axis height on the order of 8 mm, so as to produce an opening area of approximately 176 square millimeters (this and other area calculations are not precise figures because the curved walls have not been considered in calculating area). The exit opening contiguous with the chamber 44 is also generally of parallelogram shape, and has a major axis length of about 15 mm and a minor axis height of about 3 mm, for an opening area of approximately 45 square millimeters. Thus, the area of the exit opening is about one-fourth of the area of the entrance opening. This substantial reduction in cross-sectional area from the entrance opening to the exit opening will squeeze frontal air and cause it to increase in velocity as it travels through the vent 40. The adjacent scoop openings 40 on each side of the center opening are of generally similar size and dimensions, although they taper to a smaller height to better fit the narrow dimensions of the upper front section of the goggle and to improve aesthetics. It is preferred that the inlet scoops 40 have tapering shapes so that the exit openings are on the order of 50 percent or less of the area of the entrance openings.

The plurality of scoops 40 have large entrance openings which in total occupy a substantial portion of the upper front section of the frame. For example, the approximate length of the upper front section of the frame can be on the order of 160 mm as measured in a straight line from the right most end to the left most end of the six vent openings 40, and has an approximate height on the order of 8 mm to 10 mm (which height varies throughout the length of the upper section). Thus, the upper front facing section as an available area on the order of 1,600 square millimeters more or less (again, this is not a precise figure as it does not take into account the irregular shape of this section). The approximate area of the six vents 40 can be estimated as on the order of 1,040 square millimeters, more or less. Thus, over 50 percent or half of the upper front facing section is occupied by air vents, and these forward inlet vents can occupy two-thirds (⅔) of the available space, as an example. It should be understood that the specific area figures are very approximate, and were calculated using straight line dimensions rather than the actual curved dimensions, and are merely exemplary to illustrate relative sizes and areas for relative comparison purposes.

Figure 6:
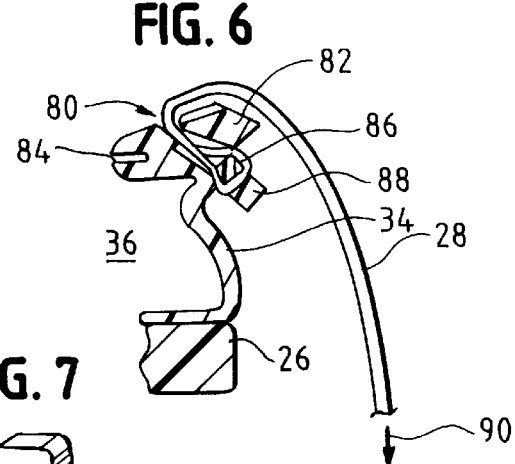
FIG. 6 is a detailed view including a cross-section of the frame taken along lines 6—6 of FIG. 2 and, in addition, illustrating the headband strap in its retained position.

FIG. 2 illustrates the goggle frame with the strap 28 of FIG. 1 being removed so as to better illustrate the side of the frame. Each frame side 34 includes a curved slot 80 which has a radius center(s) located within the center regions of the lens area and forms a compound and generally concave shape when viewed from the center regions of the goggle. By way of example, one goggle which was made had curved slots 80 on each side which are portions of an ellipse and with a radius of approximately 2 inches or about 5 centimeters (50 millimeters). The maximum curve which can be placed within the relatively narrow frame side 34 is dependent on the dimensions of the goggle. In general, the maximum curvature has a radius of about 1 inch or about 2.5 centimeters (25 millimeters). The curved slot 80 does not have to form a true arc of a circle but rather can be of compound shape such as a portion of an ellipse. The curved slot 80 is elongated and narrow, and is a defined on its inner side by a curved wall of the side frame 34. Its outer side is defined by a curved retention bar 82 which is integrally molded as a part of the flexible frame. The retention bar 82, seen best in FIGS. 2, 4 and 6, is subject to substantial forces from the stretchable strap 28 when the strap is secured around the retention bar 82. The retention bar 82 is integrally formed of the same injection molded plastic as the frame 22 and thus will flex and distort as it is pulled by the surrounding strap 28.

A peripheral groove 84 extends around the entire perimeter of the forward portions of the frame in order to releasably mount the front lens 24 in spaced relation to the wearer's eyes. This mounting groove receives the edge of the plastic lens 24 to replaceably mount the front lens. The plastic lens 24 can have projections around its edge, as is conventional, which are received within deeper recesses within the mounting groove 84 in order to secure the lens 24 within the frame. The replaceable lens 24 can be a single lens or a double lens for thermal protection, as is conventional. In addition, the lens 24 can be tinted with various colors to effect contrast characteristics.

As seen best in FIGS. 2 and 6 of the present application, the curved strap slot 80 extends through the frame from the front side to an exterior rear region of the goggle frame and defines in part the side retention bar 82. The curved slot 80 is entirely separate from the vent apertures and does not communicate with the interior space 36 of the goggle.

During assembly, the stretchable strap 28 is inserted through the fronts of the curved slots 80 on both sides and is then secured so as to not pull out when retention forces are placed on the strap. The retention mechanism for each side of the goggle can be different. As seen in FIG. 6, a terminating end 86 of the strap after being inserted through the curved slot 80 from the front to the rear of the frame is then folded over and sewn back on the strap 28 so as to form a loop at the terminating end. If the loop is sufficiently thick, it will not slip through the elongated slot 80 and can form the retention mechanism. In general, however, it is preferred that an elongated plastic retaining member 88 be located within the loop so as to better prevent the strap from pulling out through the curved slot 80.

Figure 7:
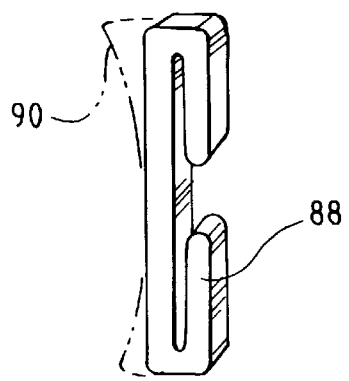
FIG. 7 is an enlarged perspective view of embodiments for a strap retention clip as seen in FIG. 6.

As illustrated in FIGS. 6 and 7, the elongated plastic retaining member 88 can take the form of a C-clip, as illustrated. Alternatively, the retaining member 88 can take the form of an O-clip or a barbell or dog-bone shape. Desirably, the retention member 88 ultimately should have an elongated curved shape which conforms with the curved slot 80 in order to not distort the flexible frame at the sides. In one embodiment, the retention clip 88 can be initially formed of straight sides provided it is made of a plastic material, such as polyethylene, which will cold flow into a curved shape 90, see FIG. 6, which matches the radius of the curved slot 80. When initially formed of a straight elongated member 88 of polyethylene material, it will initially distort the curved slot 80 and the retention bar 82, but continued pressure due to the tightening of the headband strap 28 will cause the retention member to cold flow into the curved shape 90 which is desired in order to match the curved slot 80. In a different embodiment, the retention member 88 can be formed initially with a curved radius 90 which matches the curved radius of the slot 80.

At the opposite side of the goggle frame from that illustrated in FIG. 6, the retention mechanism can be the same as illustrated or, alternatively, the strap end can be folded in a much larger loop which may include a conventional adjustment buckle (not illustrated) for user adjustment of the length of the strap. It is desired that an adjustable strap of conventional design be part of the headband strap 28 so as to allow the user to adjust the length of the strap so as to fit the goggle snugly against the users face.

Figure 5:
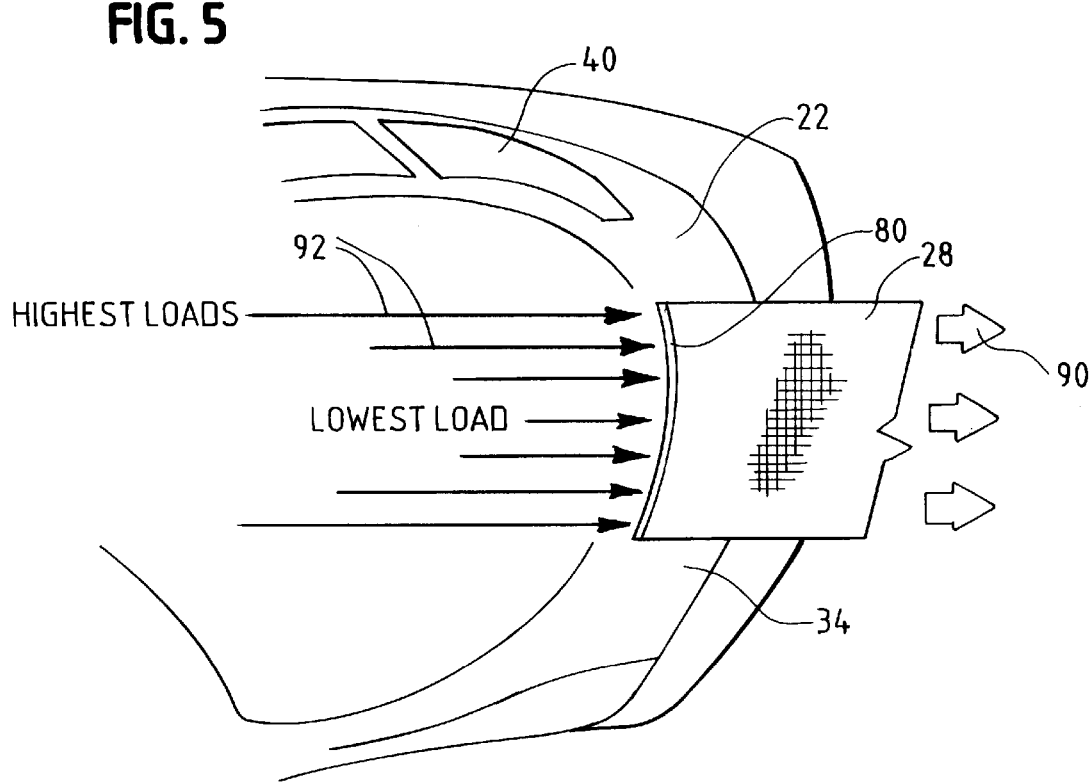
FIG. 5 is a front plane view illustration of the strap retention mechanism and headband strap and including vector arrows showing loads on the strap and frame.

The headband strap 80 is formed of a elastic woven nylon material as is conventional. When the strap 28 is placed through the curved slot 80 on both sides of the frame and is folded over or otherwise secured, then the flexible strap can be placed over a wearer's head or over a helmet, and can be snugly adjusted to be retained by the wearer's head or helmet. This creates retention forces as illustrated by the arrows 90 in FIGS. 5 and 6. Conventional slots for the headband strap are straight, and cause the retention forces to be generally uniform over the length of the slot and retention bar. A greater force exists at the center region compared to the present invention, and this tends to distort the retention bar 82 and cause undesirable wear on the strap and undesirable flexing forces on the goggle frames when using a straight sided slot. In contrast, the present invention uses a curved slot 80 in conjunction with the elastic strap so that the resulting distribution of loads is uneven over the extent of the slot 80, as is illustrated by the lengths of the vector load arrows 92 in FIG. 5. The greatest loads are at the ends of the curved slot, whereas the lowest loads are in the middle region of the curved slot. It should be understood that the lengths of the vector load arrows 92 in FIG. 5 are merely illustrative of the varying loads and do not represent precise measurements. By use of the curved slot 80 and the curved retention bar 82, distortion forces are reduced, and the goggle frame has a better fit on the head of the wearer. This is particularly desirable when the goggle is used in conjunction with a helmet where the goggle strap may be adjusted for a relatively tight fit. Also, the sides of the flexible frame are less distorted and this assists in maintaining the replaceable lens 24 within the peripheral groove 84 of the goggle frame. Further modifications and changes to the invention can be made without departing from the scope of the invention.

What is claimed is:

1. A goggle comprising:
   a frame having a top section, side sections and a bottom section for supporting the front lens in spaced relation in front of a wearer's face to define an interior space,
   a front facing vent located in a forwardly facing portion of the frame to input exterior air moving relatively towards the front lens,
   a channel located in the frame between the front facing vent and the interior space to direct the exterior air from the front facing vent to the interior space,
   dispersing means associated with the channel for dispersing the exterior air across a greater area than the front facing vent including towards an inside surface of the front lens and having a rear wall opposite the front facing vent and located in the channel for deflecting the exterior air towards the interior space and partly forwardly against an inside surface of the front lens and an inlet porous foam located in the channel between the front facing vent and the rear wall, and
   an outlet vent located in the frame for allowing air from the interior space to exit the goggle.

2. The goggle of claim 1 wherein
   an outlet porous foam having a total porosity of a first characteristic covers the outlet vent and
   the inlet porous foam has a total porosity of a different characteristic than the outlet porous foam and is located within the channel so that exterior air from the front facing vent moves through the inlet porous foam.

3. The goggle of claim 2 wherein the inlet porous foam is substantially thicker than the outlet porous foam.

4. The goggle of claim 2 wherein the inlet porous foam has a substantially different pores per volume density than the outlet porous foam.

5. The goggle of claim 1 wherein the rear wall includes a curved deflector portion which curves forwardly toward the inside surface of the front lens in order to direct some of the exterior air to have a forward component within the interior space.

6. The goggle of claim 5 wherein the curved deflector portion is located at a terminating end of the rear wall in order to redirect air flow leaving the rear of the channel with the forward component.

7. The goggle of claim 1 including an outlet porous foam located across the outlet vent and having a total porosity of different characteristic than the inlet porous foam.

8. A goggle comprising:
a front lens,
a frame having a top section, side sections and a bottom section for supporting the front lens in spaced relation in front of a wearer's face to define an interior space,
a front facing vent located in a forwardly facing portion of the frame to input exterior air moving relatively towards the front lens, and having an inlet opening of first area in the frame and spaced therefrom an exit opening of second area in the frame
a channel located in the frame between the front facing vent and the interior space to direct the exterior air from the front facing vent and through the exit opening to the interior space,
the frame includes surrounding walls from the inlet opening to the exit opening in order to define the front facing vent, at least certain of the surrounding walls being slanted with respect to frontal exterior air moving directly towards the front lens so as to deflect sideways at least portions of the frontal exterior air as it is directed into the channel, and
an outlet vent located in the frame for allowing air from the interior space to exit the goggle.

9. The goggle of claim 8 wherein the reduced area is at least 50% smaller than the greater area of the inlet opening.

10. The goggle of claim 8 wherein the frame includes at least two inlet openings in order to define the front facing vent, at least certain of the surrounding walls of one of the inlet openings being slanted in a first direction with respect to frontal exterior air moving directly towards the front lens so as to deflect sideways in the first direction at least portions of the frontal exterior air as it is directed into the channel and at least other of the surrounding walls of the second of the inlet openings being slanted in a second direction different from the first direction so as to deflect sideways in the second direction at least portions of the frontal air as it is directed into the channel, whereby the channel receives exterior air directed in different directions into the channel.

11. The goggle of claim 8 wherein the top section of the frame is formed by a solid surface which lacks any openings into the frame.

12. The goggle of claim 11 wherein the solid surface includes a smooth helmet mating section for use when the goggle is worn in conjunction with a helmet.

13. The goggle of claim 8 including a plurality of front facing vents located along an elongated region of the forwardly facing portion of the frame, and the channel is elongated and open throughout its length so that exterior air from the plurality of front facing vents will enter the open elongated channel and flow into the interior space.

14. The goggle of claim 13 wherein the outlet vent includes at least first and second outlet vents located in the bottom section of the frame, the elongated region is located in the top section of the frame and the open elongated chamber is located in the top section of the frame so that exterior air enters the top section of the frame and flows downwardly through the interior space to exit at the bottom section of the frame.

15. The goggle of claim 13 including a first plurality of front facing vents located along a first elongated region spanning one side of the frame and a second plurality of front facing vents located along a second elongated region spanning a different side of the frame, and the elongated channel spans the first and second elongated regions to form an open air chamber which spans the length of the frame.

16. A goggle comprising:
a front lens,
a frame having surrounding sections for supporting the front lens in spaced relation in front of a wearer's face to define an interior space,
a plurality of front facing air scoops spaced across a forwardly facing portion of the frame to input a large volume of exterior air moving relatively towards the front lens with at least certain of the front facing air scoops having an inlet opening in the forwardly facing portion of the frame and spaced therefrom an exit opening in the frame, the inlet opening having an area of substantially greater size than the exit opening area to thereby increase the velocity of the exterior air as it moves through said certain front facing air scoops,
dispersing means located in the frame between the plurality of front facing air scoops and the interior space and contiguous with the exit opening for substantially reducing the large volume of exterior air and dispersing the exterior air into the interior space, and
an outlet vent located in the frame for allowing air from the interior space to exit the goggle.

17. The goggle of claim 16 where at least certain of the front facing air scoops have an opening dimension of greater than 3 mm.

18. The goggle of claim 16 where at least certain of the front facing air scoops have an opening dimension of greater than 10 mm.

19. The goggle of claim 16 wherein at least certain of the front facing air scoops have an elongated shape with a major axis of longer dimension and a minor axis of shorter dimension, with the major axis being at least twice as long as the minor axis.

20. The goggle of claim 19 wherein the major axis of said certain of the front facing air scoops is greater than 10 mm and the minor axis is greater than 2 mm and forms a substantially elongated shape.

21. The goggle of claim 16 wherein the inlet opening area is at least twice the size of the exit opening area.

22. The goggle of claim 16 wherein the frame includes surrounding walls extending from the inlet opening to the exit opening, at least some of the surrounding walls being slanted with respect to frontal exterior air moving directly towards the front lens so as to deflect sideways at least portions of the frontal exterior air as it moves through the certain front facing air scoops.

23. The goggle of claim 16 wherein the dispersing means includes a deflector wall spaced behind the plurality of front facing air scoops to deflect at least a portion of the exterior air so as to have a forward component within the interior space.

24. The goggle of claim 23 wherein the deflector wall is curved toward the interior space and forwardly toward the front lens in order to deflect at least the portion of the exterior air with a forward component toward an inside surface of the front lens.

25. The goggle of claim 16 wherein the dispersing means includes a first porous foam having a total porosity of a first characteristic for substantially reducing the large volume of exterior air and a second porous foam located across the outlet vent and having a total porosity of different characteristic than the first porous foam.

26. The goggle of claim 25 wherein the total porosity of the first porous foam is at least twice as dense as the total porosity of the second porous foam.

27. A goggle comprising:

a front lens, a frame having surrounding sections for supporting the front lens in spaced relation in front of a wearer's face to define an interior space, inlet air vents formed in the frame for admitting exterior air into the interior space, a first porous foam covering the inlet air vents and having a total porosity of a first value which controls the amount of air flow through the first porous foam, outlet air vents formed in the frame for allowing air from the interior space to exit the goggle, a second porous foam different than the first porous foam and covering the outlet air vents and having a total porosity of a second value substantially different than the first value so that the amount of air flow through the second porous foam is substantially different than through the first porous foam.

28. The goggle of claim 27 wherein the total porosity of one of the first and second porous foams is at least twice as dense to air flow as the other of the first and second porous foams.

29. The goggle of claim 27 wherein one of the first and second porous foams is at least twice as thick as the other of the first and second porous foams.

30. The goggle of claim 29 wherein said one of the first and second porous foams is more than four times thicker than the other of the first and second porous foams.

31. The goggle of claim 27 wherein the inlet air vents are located in a forwardly facing portion of the frame to input exterior air moving relatively towards the front lens, and the first value for the first porous foam is at least double the second value for the second porous foam to thereby reduce the amount of air flow through the forwardly facing inlet air vents compared to the air flow through the outlet air vents.

32. The goggle of claim 31 including an open channel located in the frame between the forwardly facing inlet air vents and the interior space and the first porous foam is located within the channel to thereby disperse the exterior air flowing into the interior space.

33. The goggle of claim 32 wherein the open channel terminates in a deflector wall which redirects the air with a forward component into the interior space.

34. The goggle of claim 27 wherein the inlet air vents comprise a plurality of front facing air scoops spaced across a forwardly facing portion of the frame to input a large volume of exterior air moving relatively towards the front lens, the first porous foam being located between the plurality of front facing air scoops and the interior space, the first value of total porosity of the first porous foam being substantially greater than the second value of total porosity of the second porous foam.

35. The goggle of claim 34 wherein at least certain of the front facing air scoops have an elongated shape with a major axis of longer dimension and a minor axis of shorter dimension, with the major axis being at least twice as long as the minor axis.

36. The goggle of claim 27 wherein the frame includes a channel contiguous with the inlet air vents and open throughout its length to the interior space, and the first porous foam is located within the channel so as to span all of the inlet air vents.

37. A goggle comprising:

a front lens, a frame formed of flexible material having a top section, side sections and a bottom section for supporting the front lens in spaced relation in front of a wearer's face to define an interior space, at least one of the side sections of the frame including a flexible retention bar having curved walls defining a curved slot extending through the frame, a stretchable strap for securing the goggle to a wearer's head and extending into the curved slot so that the width of the strap extends in a curve within the curved slot, and securing means for securing the strap around the flexible retention bar so that retention forces on the strap create varying loads across the width of the curved slot to reduce distortion of the flexible frame.

38. The goggle of claim 37 wherein the curved walls have a radius center located within the front lens so as to define a generally concave curved slot with respect to a center portion of the goggle.

39. The goggle of claim 38 wherein the other of the side sections of the frame include a second flexible retention bar having second curved walls defining a second curved slot extending through the frame, second securing means for securing the strap around the second flexible retention bar, the first named curved slot and the second curved slot each being generally concave with their respective radii located within center portions of the goggle.

40. The goggle of claim 37 wherein the securing means comprises a plastic retention member capable of having a curved shape which mates with the curved slot and is locatable within the curved walls to prevent the strap from pulling through the curved slot.

41. The goggle of claim 40 wherein the plastic retention member is initially formed straight and is cold flow deformable when located within the curved walls so as to conform to the curved slot.

42. The goggle of claim 41 wherein the plastic retention material is elongated and is formed of polyethylene material.

43. The goggle of claim 40 wherein the plastic retention member is elongated and is initially formed with a curved shape, which mates with the curved walls of the curved slot.

44. The goggle of claim 37 wherein the sections of the frame have a peripheral groove for mounting a replaceable front lens, the flexible frame being manipulable so that the replaceable front lens can be inserted into and removed from the peripheral groove, and the varying loads across the width of the curved slot serving to reduce distortion of the flexible frame to thereby assist in retaining the replaceable front lens within the peripheral groove.

45. The goggle of claim 37 wherein the curved walls have a radius of about two inches or less with the radius center being located within an area of the front lens.

46. The goggle of claim 45 wherein the maximum radius of the curved walls is about one inch.

* * * * *